United States Patent [19]
Holy et al.

[11] 4,288,369
[45] Sep. 8, 1981

[54] PRODUCTION OF CYCLIC ETHERS

[75] Inventors: Norman L. Holy, Bowling Green, Ky.; Theodore E. Nalesnik, Cincinnati, Ohio

[73] Assignee: Western Kentucky University, Bowling Green, Ky.

[21] Appl. No.: 71,667

[22] Filed: Aug. 31, 1979

Related U.S. Application Data

[63] Continuation-in-part of Ser. No. 816,941, Jul. 19, 1977, abandoned.

[51] Int. Cl.³ .................. C07D 307/08; C07D 307/06; C07D 309/04; C07D 313/04
[52] U.S. Cl. .................................... 260/333; 260/338; 260/345.1; 260/346.11; 568/402
[58] Field of Search ................. 260/333, 346.11, 345.1

[56] References Cited

PUBLICATIONS

M. Bartok et al., Acta Physica et Chemica, vol. 18, (1972), No. 3-4, pp. 207-211.
W. G. Lloyd, Jour. Org. Chem., (1967), pp. 2816-2819, vol. 32.

*Primary Examiner*—Norma S. Milestone
*Attorney, Agent, or Firm*—Birch, Stewart, Kolasch & Birch

[57] ABSTRACT

A process for the preparation of cyclic ethers which comprises reacting an alkanediol in which the hydroxyl groups are separated by a chain of at least four carbon atoms in the liquid phase of a catalyst comprising a palladium salt and a copper salt, and recovering the cyclic ether thus formed by a separation step such as distillation. The reaction is carried out in a molecular oxygen gaseous atmosphere. A preferred catalyst is palladium chloride in combination with a copper salt such as cupric chloride or cupric nitrate.

18 Claims, No Drawings

PRODUCTION OF CYCLIC ETHERS

This application is a Continuation-in-Part of copending application Ser. No. 816,941, filed on July 19, 1977, now abandoned.

BACKGROUND OF THE INVENTION

This invention relates to a novel process for the preparation of cyclic ethers. More particularly, the invention is concerned with a process for effecting a cyclizing dehydration of alkanedoils in which the hydroxyl groups are separated by a chain of at least 4 carbon atoms, to form cyclic ethers which can be five, six and higher membered rings, e.g., tetrahydrofuran, tetrahydropyran, etc. The process is carried out in the presence of highly active palladium salt containing catalysts, thereby providing a practical and economical process adapted to operation on a technical scale for the conversion of diol compounds to cyclic ethers.

THE PRIOR ART

U.S. Pat. No. 2,198,374 to Bruson et al, issued on Apr. 23, 1940, teaches preparing a substituted tetrahydrofuran by the removal of one molecule of water from the corresponding 1,4-glycol at lines 3–23 in the second column on page 1. A comprehensive list of catalysts capable of such removal of the water appears at lines 20–23 in the first column on page 2 of this patent, e.g., Friedel-Crafts catalysts, $H_2SO_4$, etc.

U.S. Pat. No. 2,251,835 to Reppe et al, issued on Aug. 5, 1941, teaches preparing tetrahydrofuran by dehydrating 1,4-butylene glycol in the presence of various catalysts which promote the splitting off of water. A comprehensive list of catalysts which promote the splitting off of water appears at lines 29–53 in the left-hand column on page 1 of this patent, and includes mainly acid-acting substances, e.g., organic and inorganic acids, etc.

U.S. Pat. No. 2,251,895 to Reppe et al, issued on Aug. 5, 1941, teaches preparing tetrahydrofuran by dehydrating 1,4-butylene glycol in the presence of various metal halide catalysts, e.g., $AlCl_3$, $MgCl_2$, etc.

U.S. Pat. No. 3,006,926 to Case et al, issued on Oct. 31, 1961, teaches treating either butane-1,4-diol or pentane-1,5-diol with a sulfuric acid catalyst to obtain either tetrahydrofuran or tetrahydropyran, respectively.

Lloyd, "Journal of Organic Chemistry", Vol. 32, pgs. 2816–2819 (1967), teaches in the first full paragraph in the left-hand column on p. 2818 the oxidation of 1,4-butanediol with a $PdCl_2$ catalyst in the presence of oxygen and a copper salt. This resulted in low yields of γ-butyrolactone and probably 2-(ω-hydroxybutoxy) tetrahydrofuran. No tetrahydrofuran (i.e., unsubstituted in any manner) was reported as being produced; this is probably due to differences in operating parameters, e.g., reaction temperature.

German Auslegeschrift No. 1,043,342, issued on Nov. 13, 1958, teaches a continuous process for the preparation of tetrahydrofuran by a cyclizing dehydration of 1,4-butanediol in the presence of a sulfuric acid catalyst.

OBJECTS OF THE INVENTION

An object of the present invention is to provide a practical and economic process which is adapted to the technical scale production of cyclic ethers by a cyclizing dehydration of an alkanediol in which the hydroxyl groups are separated by a chain of at least four carbon atoms, carried out in the presence of a catalyst which is markedly superior to those known heretofore.

The cyclizing dehydration of the above-described alkanediols for the production of cyclic ethers is a known reaction, and it has been proposed to bring said reaction within the field of practical utility by executing it in the presence of catalysts. Several catalysts for this purpose are those of an acidic character, particularly sulfuric acid and other strong mineral acids such as hydrochloric acid, phosphoric acid, etc..

While the processes depending upon the employment of acid catalysts have the advantage of permitting the use of simple apparatus, they are still quite undesirable from a commercial standpoint. Under the reaction conditions employed in the prior art, the acidic reaction mixtures have a strongly corrosive action on the reaction equipment, making necessary the use of costly non-corrosive apparatus or requiring periodic replacement of the initially less costly apparatus. Many processes of this kind make use of sulfuric acid as the catalyst and involve elimination of the acid, after the cyclizing dehydration is terminated, e.g., by precipitating it from the reaction mixture in the form of its calcium or barium salts. Such separation is, however, always incomplete, and there remains in the reaction mixture substantial amounts of non-precipitatable salts of organic sulfuric acid compounds which are only separated during distillation and cause contamination of the desired product. Besides the inconveniences mentioned, executing the reactions in the presence of acid catalysts results in material losses and contaminated products due to occurrence of side reactions, e.g., a 1,2-dehydration of 2,5-hexanediol, which, as well as the desired main reaction, are accelerated by the acids.

The present invention provides a process which eliminates the drawbacks and inconveniences of the known process for effecting a cyclizing dehydration of alkanediols. The superior process for the production of cyclic ethers described herein is based on the use of a catalyst which accelerates the rate of reaction to at least as great an extent as any of the catalysts previously employed, is relatively inexpensive and readily available, and is adapted to be easily and completely removed after completion of the reaction without any destruction of the reaction product. This process results in the attainment of excellent yields of the desired reaction products, the reaction proceeding smoothly and rapidly at considerably lower temperatures and under lower pressures than are necessary when operating in the presence of the known acidic catalysts. Reuse of the recovered catalyst can be accomplished for several hundreds of runs.

DETAILED DESCRIPTION OF THE INVENTION

The process of the invention is applicable broadly to the cyclizing dehydration of an open chain diol which has a minimum of four carbon atoms in said chain separating the hydroxyl groups. The reaction involved in the production of the cyclic ether is shown, with respect to an open chain diol which is a 1,4-diol:

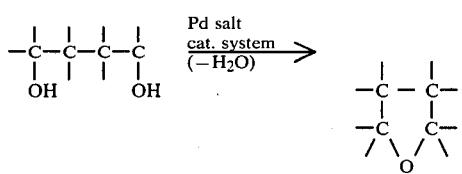

The reaction mechanism involved is believed to be as follows:

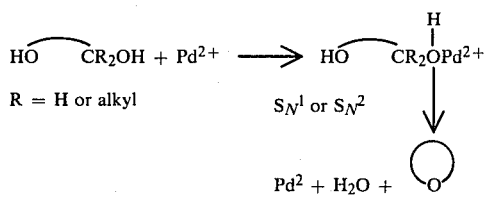

THE CATALYST EMPLOYED

It has been found that the cyclizing dehydration of said open chain diols to form cyclic ethers can be made to proceed at a practical rapid rate with resultant high yield of the desired cyclic ether if it is conducted in the liquid phase in the presence of a palladium salt and a copper salt. If neither of these salts contains the chloride ion, then it must also be supplied to the catalyst system. In addition to the metal salts, the catalyst system also contains oxygen in the free state, i.e., gaseous oxygen. The function of the copper salt is to reoxidize the free palladium metal produced by a competing oxidative reaction. An example of this function is shown in the following reaction scheme:

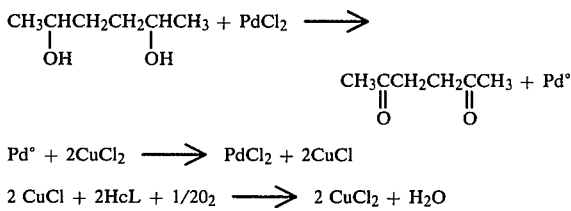

$Pd° + 2CuCl_2 \longrightarrow PdCl_2 + 2CuCl$ $2\,CuCl + 2HcL + 1/2O_2 \longrightarrow 2\,CuCl_2 + H_2O$ The palladium salt employed in the catalyst system may be either an inorganic or an organic salt, and the cation thereof may be in any desired valence state. Examples of inorganic salts are the various palladium halides and palladium sulfates. Double salts can also be employed, for example, $K_2PdCl_4(2KCl.PdCl_2)$. The palladium salt can also be in the form of a complex salt, e.g., of the Werner type. Examples thereof are palladoammine salts, e.g., $Pd(NH_3)_2Cl_2$ and $Pd(SO_3)(NH_3)_3$. It is not necessary that the palladium salt be added in a preformed state to the reaction system. A palladium salt precursor can be employed, e.g., PdO, which can be converted to a palladium salt by the other components present in the reaction system, e.g., $CuCl_2$. Some illustrative examples of organic salts are palladium acetylacetonate and palladium acetate. The valence state of the palladium in the palladium salt can be either $Pd^+$ or $Pd^{++}$. In the case of a palladous salt, e.g., PdCl, it will of course be quickly oxidized to $PdCl_2$ because of the presence of $O_2$ in the catalyst system. The preferred palladium salt, because of cheapness and simplicity of use in this process, is palladium chloride, $PdCl_2$. The palladium is employed in an amount of about 0.45 to 0.71 grams of palladium per mole of alkanediol.

The copper salt employed in the catalyst system may again be either an inorganic or an organic salt, and the copper cation as well as the anion thereof may be in any desired valence state. Examples of such salts are copper chloride [$CuCl_2$], copper nitrate [$Cu(NO_3)_2$] and copper sulfate [$CuSO_4$]. Double copper salts can also be employed, for example, $Cu(NH_4)_2(SO_4)_2$. Also, the copper salt can be in the form of a complex salt, e.g., of the Werner type. Examples thereof are $Cu(NH_3)_2Cl_2$ and $Cu(NH_3)_4SO_4$. Examples of organic salts are copper acetate and copper acetylacetonate. The valence state of the copper in the copper salt can be either $Cu^+$ or $Cu^{++}$. In the case of a cuprous salt, e.g., CuCl, it will of course be quickly oxidized to $CuCl_2$ because of the presence of $O_2$ in the catalyst system. Mixtures of copper salts can also be employed. If neither the palladium nor the copper salt employed contain the chloride anion, then this must be supplied to the catalyst system in the form of another salt which does contain said chloride anion, e.g., an alkali metal chloride such as sodium chloride or potassium chloride. The chloride ion is employed in an amount of about 0.30 to 1.1 grams of chloride per mole of alkane diol. The preferred copper salt, because of cheapness and simplicity of use is copper chloride ($CuCl_2$). The copper is employed in an amount of about 0.03 to 1.2 grams of copper per mole of alkanediol.

This group of catalysts possesses some peculiar property, not at present understood, which enables then to greatly increase the rate of a liquid phase reaction involving the cyclizing dehydration of an open chain diol.

The high catalytic activity of this group of catalysts makes it attractive to employ them in the process of the invention since only small amounts are required in order to obtain a substantial yield of the cyclic ether in a relatively short period of time. The actual amount of catalyst needed in the process, however, is dependent upon a number of factors, including the particular system employed, the particular open chain diol employed, the water content of the reaction mixture and the operating conditions employed. Satisfactory results may be obtained with catalyst concentrations in the reaction mixture of from one tenth of one percent to one percent by weight. If advantageous and desired, more or less than this amount may be used.

The catalysts employed in the process generally are hydrolyzable compounds when in the presence of water. Furthermore, the catalytic activity thereof is considerably reduced when they are in a hydrolyzed condition, and larger amounts of catalyst are required to effect the reaction when the reactants contain appreciable amounts of water as compared to when they are substantially dry. Also, the hydrogen halide liberated by the hydrolysis of the metal salts of the catalyst composition may combine with the open chain diol compound to form by-products which may be troublesome to remove from the desired product. It is therefore preferable for the open chain diol used in the process of the invention to be in a substantially anhydrous condition. The same is of course true with respect to the metal salts employed in the catalyst system.

The catalyst system components are left behind in the residues obtained by working up the reaction mixture, after termination of the reaction, to recover the cyclic ether product therefrom. This recovery of the reaction product may be effected in any suitable manner. In most cases, it is conveniently done by distillation, preferably under a subatmospheric pressure. The catalyst system components contained in the distillation residues may be reutilized as catalysts in the process by returning them, or any suitable portion thereof, to the reaction vessel. The following data is illustrative of the number of times such reuse can be effected.

| Reaction Involved | Catalytic Cycles |
|---|---|
| (1) 1,6-Hexanediol → Oxacycloheptane | >300 |
| (2) 1,5-Pentanediol →Tetrahydropyran | >500 |
| (3) 2,5-Hexanediol →2,5-Dimethyltetrahydrofuran | >500 |

THE OPEN CHAIN DIOL REACTANT

The open chain diols which may be employed in the process of this invention are open chain primary, secondary, and tertiary 1,4-butanediols, pentanediols and hexanediols. The carbon atoms of the open chain may be either unsubstituted or substituted. Examples of substituents are alkyl, aryl, cycloaryl, or aralkyl. Examples of representative unsubstituted diols are, among others, 1,4-butanediol, 1,5-pentanediol, 1,6-hexanediol and 2,5-hexanediol. Examples of representative substituted diols are 2,5-dimethylhexane-2,5-diol; 7,10-dimethylhexadecane-7,10-diol; tetraphenylbutanediol-1,4, etc.

OPERATING PARAMETERS

The reaction is conducted at temperatures from about 150° C. to 300° C. The reaction begins immediately upon contact of the open chain diol with the catalyst and, while it may initially be slow at the low temperatures, the reaction soon becomes vigorous with a resultant increase in temperature of the reaction mixture. In general, the reaction may be completed by heating to the desired reaction temperature. In cases where higher reaction temperatures than the normal boiling point of the reaction mixture are used, it is desirable to maintain a pressure on the reaction mixture at least equal to the total vapor pressure of said reaction mixture at the operating temperature, since the desired reaction occurs in the liquid phase.

The process of the invention may be executed in any suitable size or shape of reaction vessel. When metal reaction chambers or vessels are employed, the interior surface of the reaction vessel should consist of a material which will lose no substantial amount of iron by contact with the reaction mixture under the reaction conditions. Suitable iron-containing metal surfaces which can be in contact with the reaction mixture during the execution and lose no or practically no iron are the relatively inexpensive and well-known chromium-nickel-steel alloy such as V$_2$A steel. The process may, if desired, be executed in ordinary iron or steel reaction vessels which have been lined with enamel, glass or some like non-corrosive material.

The temperature to be employed in any particular case will depend to a certain extent upon the nature and reactivity of the particular open chain diol employed, the particular catalyst system employed, the desired time of contact of said diol with the catalyst system employed, etc. It is an advantage of our process that it can in the great majority of cases be satisfactorily executed at a maximum temperature of about 150° C. under normal atmospheric pressure. In general, temperatures in the practical operating range of 150° C. to 200° C. are suitable. Normally the reaction can be conducted at atmospheric pressure. However, since the reaction takes place in the liquid phase, superatmospheric pressure may be employed, if necessary, to maintain the diol in the liquid state.

The process of the invention may be executed in a variety of manners, and is adaptable to batch-wise, intermittent or continuous operation. The reaction may be allowed to proceed satisfactorily with the reaction mixture contained in a vessel fitted with heating and cooling means as well as suitable condensing means, such as a reflux condenser, for condensing and returning any vapors which may be evolved. In order to assure completion of the reaction mixture, the reaction mixture is heated for a period of time during which samples may be withdrawn and analyzed to determine when the reaction is substantially complete. The unreacted component of the reaction mixture and the products of the reaction may be separated in any suitable manner, such as by distillation.

For continuous operation the diol would be added to the reaction vessel continuously while the product ether is being distilled. Since the ethers have boiling points ca. 100° lower than the diols, product separation is easily accomplished and the products are virtually uncontaminated with starting diol even with very simple apparatus. See German Auslegeschrift No. 1,043,342 referred to above.

The following examples are given merely as illustrative of the present invention, and are not to be considered as limiting. Unless otherwise indicated, the percentages therein and throughout the application are by weight.

EXAMPLES 1-16

Oxidations were carried out in a standard, low-pressure catalytic apparatus (Parr Instrument Co., Model 3911). In a typical run a 500 ml glass reactor vessel was charged with 30.0 g of diol along with the desired amounts of catalyst, the system sealed, purged three times with oxygen, then pressurized to 60 psig oxygen pressure and rapidly brought to the desired temperature by means of a heating mantle. The temperature was established by standardizing the mantle and variac without pressurizing the system. After the desired time had passed, the reactor was cooled and the contents were collected for analysis.

Product separations and yields were determined by distillation and/or gas chromatography. Product identities were determined by ir, nmr, and mass spectral data.

Examples 1 and 3 in Table 1 are merely for illustrative purposes, i.e., to show the effect of a temperature below 150° C. upon the nature of the product obtained and the yield thereof.

TABLE 1

| | | Reactions of Diols With Palladium Catalysts | | | | |
|---|---|---|---|---|---|---|
| Ex. | Diol | Catalyst | Temp °C. | Time (hr) | Conversion (%) | Ether (%) a | Other (%) |
| 1 | 1,4-butanediol | b | 125 | 24 | 42 | tetrahydrofuran (40) | trace oxidation |

TABLE 1-continued

Reactions of Diols With Palladium Catalysts

| Ex. | Diol | Catalyst | Temp °C. | Time (hr) | Conversion (%) | Ether (%) a | Other (%) |
|---|---|---|---|---|---|---|---|
| 2 | 1,4-butanediol | c | 150 | 6 | 97 | tetrahydrofuran (95) | — |
| 3 | 2,5-hexanediol | b | 100 | 24 | 52 | 2,5-dimethyltetra hydrofuran (35) | 2,5-hexanedione (15) |
| 4 | 2,5-hexanediol | c | 150 | 6 | 97 | 2,5-dimethyltetra hydrofuran (82-92) | — |
| 5 | 2,5-hexanediol | d | 150 | 6 | 40 | 2,5-dimethyltetra hydrofuran (39) | — |
| 6 | 2,5-dimethylhexane-2,5-diol | b | 150 | 6 | 90 | 2,2,5,5,-tetramethyl dihydrofuran (70) | unidentified |
| 7 | 1,5-pentanediol | b | 150 | 6 | 100 | tetrahydropyran (75-80) | unidentified polymer |
| 8 | 1,5-pentanediol | c | 150 | 6 | 68 | tetrahydropyran (58) | unidentified polymer |
| 9 | 1,6-hexanediol | b | 150 | 24 | 63 | oxacycloheptane (10) | 1,7-dioxacyclotetra-decane (48) |
| 10 | 1,6-hexanediol | c | 150 | 24 | 56 | oxacycloheptane (8) | 1,7-dioxacyclotetra-decane (35) |
| 11 | 2,5-hexanediol | e | 150 | 6 | — | 2,5-dimethyltetra-hydrofuran (79) | — |
| 12 | 1,4-butanediol | f | 150 | 6 | — | tetrahydrofuran (32) | — |
| 13 | 1,4-butanediol | g | 150 | 6 | — | tetrahydrofuran (5) | — |
| 14 | 1,4-butanediol | h | 150 | 6 | — | tetrahydrofuran (43) | — |
| 15 | 1,4-butanediol | i | 150 | 4 | — | tetrahydrofuran (70) | — |
| 16 | 1,4-butanediol | j | 150 | 4 | — | tetrahydrofuran (61) | — | a Yields are based on mmol starting diol even when the conversion is 100%.
b 0.047 M in $PdCl_2$ and 0.063 M in $CuCl_2$.
c 0.047 M in $PdCl_2$, 0.063 M in $CuCl_2$, and 0.09 M in $Cu(NO_3)_2$.
d 0.047 M in $PdCl_2$ and 0.09 M in $Cu(NO_3)_2$.
e 0.047 M in $PdCl_2$, 0.11 M in NaCl.
f 0.063 M in $CuCl_2$, 0.075 M in KCl.
g 0.042 M in $NiCl_2 \cdot 6H_2O$, 0.086 M in KCl.
h 0.024 M in $K_2PtCl_4$.
i 0.047 M in $PdCl_2$, 0.052 M in $CuSO_4$.
j 0.047 M in $PdCl_2$, 0.068 M in $Cu(OAc)_2$.

Example 11 in Table 1 is a comparative example for the purpose of demonstrating that, in the absence of a copper salt in the catalyst system the reaction is appreciably slower. The closest Example (4) with copper catalyst had a yield as high as 92%; Example 11 without copper catalyst had a yield of only 79%.

Example 12 in Table 1 is a comparative example for the purpose of demonstrating that, in the absence of a palladium salt in the catalyst system, the reaction is extremely slow. The closest Example (2) with palladium catalyst had a yield of 95%; Example 12 without palladium catalyst had a yield of only 32%.

Example 13 in Table 1 is for the purpose of demonstrating that the nickel salt catalyst (of the prior art) is a very poor catalyst for converting 1,4-butanediol to tetrahydrofuran.

Example 14 in Table 1 demonstrates that a $Pt^{+2}$ containing salt is a fairly good catalyst for the reaction.

Example 15 in Table 1 demonstrates the use of copper sulfate in the catalyst system in conjunction with palladium chloride.

Example 16 in Table 1 is similar with respect to the use of copper acetate in conjunction with palladium chloride.

In order to illustrate the use of an organic salt of palladium in the catalyst system, the following example was carried out:

EXAMPLE 17

Palladium acetylacetonate was added to 30 grams of 1,4-butanediol in an amount sufficient to make the solution 0.047 M in palladium. Thereafter cupric chloride was added to the foregoing solution in an amount sufficient to make the solution 0.063 M in copper chloride. Heating this solution to a temperature of 140° C. and maintaining it at this temperature did not result in the formation of any tetrahydrofuran. However, by heating said solution to a temperature of 150° C. and maintaining it at this temperature, 15 ml. of tetrahydrofuran was formed in 15 minutes.

In order to illustrate the use of copper sulfate in the catalyst system at a level identical with that of $CuCl_2$ in Example 1, the following example was carried out:

EXAMPLE 18

First, 30 grams of 1,4-butanediol was added to 0.063 M copper sulfate ($CuSO_4$) solution, and the solution then heated to 150° C. and maintained at this temperature. Thereafter there was added to this solution sufficient KCl to yield a solution of 0.1 M in chloride, and additionally palladium chloride ($PdCl_2$) was also added to said solution to yield a solution 0.047 M in palladium. In twenty minutes 10 ml. of tetrahydrofuran had distilled off.

The invention being thus described, it will be obvious that the same may be varied in many ways. Such variations are not to be regarded as a departure from the spirit and scope of the invention, and all such modifications are intended to be included within the scope of the following claims.

We claim:

1. A process for the preparation of an unsubstituted cyclic ether which comprises reacting an unsubstituted alkanediol in which the hydroxyl groups are separated by a chain of at least four carbon atoms in the liquid phase, in a molecular oxygen gaseous atmosphere, at a temperature of from about 150° C. to 300° C. in the presence of a catalytic amount of a catalyst comprising about 0.45 to 0.71 grams of palladium in a palladium salt, about 0.30 to 1.2 grams of copper in a copper salt and about 0.30 to 1.1 grams of chloride ion, all per mole of alkanediol.

2. A process as recited in claim 1 in which the palladium salt is palladium chloride.

3. A process as recited in claim 2 in which the copper salt is selected from the group consisting of cupric chloride, cupric nitrate and mixtures thereof.

4. A process as recited in claim 1 in which the catalyst concentration in the reaction mixture is in the range from about 0.1 to 1% by weight thereof.

5. A process for the preparation of an unsubstituted cyclic ether which comprises reacting an unsubstituted alkanediol selected from the group consisting of 1,4-butanediol, 1,5-pentanediol, and 1,6-hexanediol in the liquid phase, in a molecular oxygen gaseous atmosphere, at a temperature of from about 150° C. to 300° C. in the presence of a catalytic amount of a catalyst comprising about 0.45 to 0.71 grams of palladium in a palladium salt, about 0.30 to 1.2 grams of copper in a copper salt and about 0.30 to 1.1 grams of chloride ion, all per mole of alkanediol.

6. A process as recited in claim 5 in which the palladium salt is palladium chloride.

7. A process as recited in claim 6 in which the copper salt is selected from the group consisting of cupric chloride, cupric nitrate and mixtures thereof.

8. A process as recited in claim 5 in which the catalyst concentration in the reaction mixture is in the range from about 0.1 to 1% by weight thereof.

9. A process for the preparation of tetrahydrofuran which comprises reacting 1,4-butanediol in the liquid phase, in a molecular oxygen gaseous atmosphere, at a temperature of from about 150° C. to 300° C. in the presence of a catalytic amount of a catalyst comprising palladium chloride and a copper salt wherein palladium is present in an amount of about 0.45 to 0.71 grams, copper is present in an amount of about 0.30 to 1.2 grams and chloride is present in an amount of about 0.30 to 1.1 grams, all per mole of butanediol.

10. A process as recited in claim 9 in which the copper salt is cupric chloride, cupric nitrate or a mixture thereof.

11. A process for the preparation of tetrahydropyran which comprises reacting 1,5-pentanediol in the liquid phase, in a molecular oxygen gaseous atmosphere, at a temperature of from about 150° C. to 300° C. in the presence of a catalytic amount of a catalyst comprising palladium chloride and a copper salt wherein palladium is present in an amount of about 0.45 to 0.71 grams, copper is present in an amount of about 0.30 to 1.2 grams and chloride is present in an amount of about 0.30 to 1.1 grams, all per mole of butanediol.

12. A process as recited in claim 11 in which the copper salt is cupric chloride, cupric nitrate or a mixture thereof.

13. A process for the preparation of 2,5-dimethyltetrahydrofuran which comprises reacting 2,5-hexanediol in the liquid phase, in a molecular oxygen gaseous atmosphere, at a temperature of from about 150° C. to 300° C. in the presence of a catalytic amount of a catalyst comprising palladium chloride and a copper salt wherein palladium is present in an amount of about 0.45 to 0.71 grams, copper is present in an amount of about 0.30 to 1.2 grams and chloride is present in an amount of about 0.30 to 1.1 grams, all per mole of butanediol.

14. A process as recited in claim 13 in which the copper salt is cupric chloride, cupric nitrate or a mixture thereof.

15. A process for the preparation of 2,2,5,5-tetramethyldihydrofuran which comprises reacting 2,5-dimethylhexane-2,5-diol in the liquid phase, in a molecular oxygen gaseous atmosphere, at a temperature of from about 150° C. to 300° C. in the presence of a catalytic amount of a catalyst comprising palladium chloride and a copper salt wherein palladium is present in an amount of about 0.45 to 0.71 grams, copper is present in an amount of about 0.30 to 1.2 grams and chloride is present in an amount of about 0.30 to 1.1 grams, all per mole of butanediol.

16. A process as recited in claim 15 in which the copper salt is cupric chloride, cupric nitrate or a mixture thereof.

17. A process according to claim 1, wherein said chloride ion is the anion of said palladium or copper salt.

18. A process according to claim 1, wherein said chloride ion is supplied as the anion of a salt other than said palladium and copper salt.

* * * * *